United States Patent
Le Bouteiller et al.

(10) Patent No.: US 10,208,124 B2
(45) Date of Patent: Feb. 19, 2019

(54) ANTI-CD160 SPECIFIC ANTIBODIES FOR THE TREATMENT OF EYE DISORDERS BASED ON NEOANGIOGENESIS

(71) Applicant: INSERM (Institut National de la Sante et de la Recherche Medicale), Paris (FR)

(72) Inventors: Philippe Le Bouteiller, Toulouse (FR); Armand Bensussan, Paris (FR)

(73) Assignees: INSERM (INSTITUT NATIONAL DE LA SANTE ET DE LA RECHERCHE MEDICALE), Paris (FR); MABLIFE, Evry (FR)

( * ) Notice: Subject to any disclaimer, the term of this patent is extended or adjusted under 35 U.S.C. 154(b) by 51 days.

(21) Appl. No.: 14/728,253

(22) Filed: Jun. 2, 2015

(65) Prior Publication Data

US 2015/0344572 A1 Dec. 3, 2015

Related U.S. Application Data

(63) Continuation of application No. 13/697,699, filed as application No. PCT/EP2011/058777 on May 27, 2011, now Pat. No. 9,045,544.

(60) Provisional application No. 61/349,271, filed on May 28, 2010.

(51) Int. Cl.
| | | |
|---|---|---|
| *C07K 16/28* | (2006.01) | |
| *C07K 16/22* | (2006.01) | |
| *A61K 39/395* | (2006.01) | |
| *A61K 9/00* | (2006.01) | |
| *A61K 39/00* | (2006.01) | |

(52) U.S. Cl.
CPC ........ *C07K 16/2896* (2013.01); *A61K 9/0019* (2013.01); *A61K 9/0048* (2013.01); *A61K 39/3955* (2013.01); *C07K 16/22* (2013.01); *C07K 16/2803* (2013.01); *A61K 2039/505* (2013.01); *A61K 2039/507* (2013.01); *C07K 2317/622* (2013.01); *C07K 2317/73* (2013.01)

(58) Field of Classification Search
CPC ............... C07K 16/22; C07K 16/2803; C07K 16/2896; C07K 2317/14; C07K 2317/75; C07K 2317/622; C07K 2317/624; C07K 2317/626; C07K 2317/54; C07K 2317/55; C07K 2317/73; A61K 39/3955; A61K 2039/505; A61K 2039/507; A61K 9/0019; A61K 9/0048

See application file for complete search history.

(56) References Cited

U.S. PATENT DOCUMENTS

| 6,884,879 B1 | 4/2005 | Baca et al. | |
| 8,444,978 B2 * | 5/2013 | Bensussan | ......... C07K 16/2803 424/139.1 |
| 2009/0317401 A1 * | 12/2009 | Bensussan | ......... C07K 16/2803 424/144.1 |

FOREIGN PATENT DOCUMENTS

| EP | 2186529 | 5/2010 |
| WO | 2006/015886 | 2/2006 |

OTHER PUBLICATIONS

Roitt et al in Immunology second edition, Gower Medical Publishing New York 1989, p. 5.8 and 5.9.*
S. Chabot et al., The Journal of Experimental Medicine, Apr. 11, 2011, pp. 973-986.
International Search Report in PCT/EP2011/058777, dated Aug. 19, 2011.
P. Fons et al., "Soluble HLA-G1 inhibits angiogenesis through an apoptotic pathway and by direct binding to CD160 receptor expressed by endothelial cells," Blood, 108(8):2608-2615 (2006) XP002530233.
Yu et al., "Interaction between Bevacizumab and Murine VEGF-A: A Reassessment," Investigative Ophthalmology & Visual Science, 49(2):522-527 (2008).
Stancovski et al., "Mechanistic aspects of the opposing effects of monoclonal antibodies to the ERBB2 receptor on tumor growth," Proc. Natl. Acad. Sci. USA, 88:8691-8695 (1991).
Riemer et al., "Matching of trastuzumab (Herceptin) epitope mimics onto the surface of Her-2/neu—a new method of epitope definition," Mol. Immunol., 42:1121-1124 (2005).
Webster's II New Riverside University Dictionary, p. 933 (1984).
Petrukhin et al., "New therapeutic targets in atrophic age-related macular degeneration," Expert Opin. Ther. Target, 11 (5):625-639 (2007).

* cited by examiner

*Primary Examiner* — Phuong Huynh
(74) *Attorney, Agent, or Firm* — McAndrews, Held & Malloy, Ltd.

(57) ABSTRACT

The present invention relates to the use of at least one anti-CD 160 antibody, preferably a compound selected from CL1-R2 monoclonal antibody (which may be obtained by the hybridoma CNCM 1-3204), its conservative fragments and its conservative derivatives, for preparing a drug designed to treat neovascular eye diseases.

13 Claims, 6 Drawing Sheets
Specification includes a Sequence Listing.

```
SEQUENCE LISTING

<160> NUMBER OF SEQ ID NOS: 2

<210> SEQ ID NO 1
<211> LENGTH: 1361
<212> TYPE: DNA
<213> ORGANISM: Homo sapiens
<220> FEATURE:
<221> NAME/KEY: CDS
<222> LOCATION: (216)..(758)

<400> SEQUENCE: 1
cagtctgaga acaagaaaga agaacttctg tctcgagggt ctcactgtca accaggccag      60
agtgcagtga agatcatacc tcactacatc cgtgaactcc cgggctcctc ccacctaagt     120
ctcttgagta gctgggactt caggagactg aagccaagga taccagcaga gccaacattt     180
gcttcaagtt cctgggcctg ctgacagcgt gcagg atg ctg ttg gaa ccc ggc        233
                                        Met Leu Leu Glu Pro Gly
                                        1               5 aga ggc tgc tgt gcc ctg gcc atc ctg ctg gca att gtg gac atc cag       281
Arg Gly Cys Cys Ala Leu Ala Ile Leu Leu Ala Ile Val Asp Ile Gln
         10                  15                  20 tct ggt gga tgc att aac atc acc agc tca gct tcc cag gaa gga acg       329
Ser Gly Gly Cys Ile Asn Ile Thr Ser Ser Ala Ser Gln Glu Gly Thr
     25                  30                  35 cga cta aac tta atc tgt act gta tgg cat aag aaa gaa gag gct gag       377
Arg Leu Asn Leu Ile Cys Thr Val Trp His Lys Lys Glu Glu Ala Glu
 40                  45                  50 ggg ttt gta gtg ttt ttg tgc aag gac agg tct gga gac tgt tct cct       425
Gly Phe Val Val Phe Leu Cys Lys Asp Arg Ser Gly Asp Cys Ser Pro
55                  60                  65                  70 gag acc agt tta aaa cag ctg aga ctt aaa agg gat cct ggg ata gat       473
Glu Thr Ser Leu Lys Gln Leu Arg Leu Lys Arg Asp Pro Gly Ile Asp
                 75                  80                  85 ggt gtt ggt gaa ata tca tct cag ttg atg ttc acc ata agc caa gtc       521
Gly Val Gly Glu Ile Ser Ser Gln Leu Met Phe Thr Ile Ser Gln Val
             90                  95                  100 aca ccg ttg cac agt ggg acc tac cag tgt tgt gcc aga agc cag aag       569
Thr Pro Leu His Ser Gly Thr Tyr Gln Cys Cys Ala Arg Ser Gln Lys
         105                 110                 115 tca ggt atc cgc ctt cag ggc cat ttt ttc tcc att cta ttc aca gag       617
```

-continued

```
              Ser Gly Ile Arg Leu Gln Gly His Phe Phe Ser Ile Leu Phe Thr Glu
                  120                 125                 130 aca ggg aac tac aca gtg acg gga ttg aaa caa aga caa cac ctt gag      665
Thr Gly Asn Tyr Thr Val Thr Gly Leu Lys Gln Arg Gln His Leu Glu
135                 140                 145                 150 ttc agc cat aat gaa ggc act ctc agt tca ggc ttc cta caa gaa aag      713
Phe Ser His Asn Glu Gly Thr Leu Ser Ser Gly Phe Leu Gln Glu Lys
                155                 160                 165 gtc tgg gta atg ctg gtc acc agc ctt gtg gcc ctt caa gct ttg          758
Val Trp Val Met Leu Val Thr Ser Leu Val Ala Leu Gln Ala Leu
                170                 175                 180 taagccttgt gccaaaagaa acttttaaaa cagctacagc aagatgagtc tgactatggc    818
ttagtatctt tctcattaca ataggcacag agaagaatgc aacagggcac aggggaagag    878
atgctaaata taccaagaat ctgtggaaat ataagctggg gcaaatcagt gtaatccttg    938
actttgctcc tcaccatcag ggcaaacttg ccttcttccc tcctaagctc cagtaaataa    998
acagaacagc tttcaccaaa gtttcctccc tcttcatcaa catagtaaaa taagtcaaac   1058
aaaatgagaa caccaaattt tgggggaata aatttttatt taacactgca aaggaaagag   1118
agagaaaaca agcaaagata ggtaggacag aaaggaagac agccagatcc agtgattgac   1178
ttggcatgaa aatgagaaaa tgcagacaga cctcaacatt caacaacatc catacagcac   1238
tgctggagga agaggaagat ttgtgcagac caagagcacc acagactaca actgcccagc   1298
ttcatctaaa tacttgttaa cctctttggt catttctctt tttaaataaa tgcccatagc   1358
agt                                                                  1361
```

<210> SEQ ID NO 2
<211> LENGTH: 181
<212> TYPE: PRT
<213> ORGANISM: Homo sapiens

<400> SEQUENCE: 2

```
Met Leu Leu Glu Pro Gly Arg Gly Cys Cys Ala Leu Ala Ile Leu Leu
1               5                   10                  15

Ala Ile Val Asp Ile Gln Ser Gly Gly Cys Ile Asn Ile Thr Ser Ser
                20                  25                  30

Ala Ser Gln Glu Gly Thr Arg Leu Asn Leu Ile Cys Thr Val Trp His
            35                  40                  45

Lys Lys Glu Glu Ala Glu Gly Phe Val Val Phe Leu Cys Lys Asp Arg
        50                  55                  60

Ser Gly Asp Cys Ser Pro Glu Thr Ser Leu Lys Gln Leu Arg Leu Lys
65                  70                  75                  80

Arg Asp Pro Gly Ile Asp Gly Val Gly Glu Ile Ser Ser Gln Leu Met
                85                  90                  95

Phe Thr Ile Ser Gln Val Thr Pro Leu His Ser Gly Tyr Gln Cys
                100                 105                 110

Cys Ala Arg Ser Gln Lys Ser Gly Ile Arg Leu Gln Gly His Phe Phe
            115                 120                 125

Ser Ile Leu Phe Thr Glu Thr Gly Asn Tyr Thr Val Thr Gly Leu Lys
        130                 135                 140

Gln Arg Gln His Leu Glu Phe Ser His Asn Glu Gly Thr Leu Ser Ser
145                 150                 155                 160
```

```
Gly Phe Leu Gln Glu Lys Val Trp Val Met Leu Val Thr Ser Leu Val
            165                 170                 175
Ala Leu Gln Ala Leu
            180
```

ANTI-CD160 SPECIFIC ANTIBODIES FOR THE TREATMENT OF EYE DISORDERS BASED ON NEOANGIOGENESIS

The present application is filed as a continuation application of U.S. patent application Ser. No. 13/697,699, which was filed Jan. 17, 2013, which was filed pursuant to 35 U.S.C. 371 as a U.S. National Phase application of International Patent Application No. PCT/EP2011/058777, which was filed May 27, 2011, claiming the benefit of priority to U.S. Provisional Patent Application No. 61/349,271, which was filed on May 28, 2010. The entire text of the aforementioned applications is incorporated herein by reference in its entirety.

The present invention relates to the use of at least one anti-CD 160 antibody, preferably a compound selected from CL1-R2 monoclonal antibodies (which may be obtained by the hybridoma CNCM 1-3204), its conservative fragments and its conservative derivatives, for treating and/or preventing neovascular eye diseases.

Ocular angiogenesis, a leading cause of vision loss in the world, occurs in two main compartments of the eye: retina and cornea.

Retinal diseases involving abnormal neo vasculature have an increasing incidence both in the rich and poor countries. In the rich countries, diabetic retinopathies, retinopathy of prematurity and Age Related Macular Degenerations (AMDs) complicated by abnormal neovessels constitute a huge economic burden as well as the two major causes of low vision and legal blindness worldwide.

Abnormal corneal neovascularizations complicating corneal infections or corneal grafts (performed in patients afflicted by inherited corneal dystrophies or by environmental insults) constitute also an important public health burden both in term of treatments costs and in term of proper integration of the affected patients in the work force and in a normal social network. The market size for age-related macular degeneration and diabetic retinopathy is huge. Although important in term of competitive market, with research studies in constant development, pathological corneal neovascularizations correspond also to a crucial ensemble of diseases that prevents the maintenance of transparent corneal graft or even prevent the possibility to perform corneal graft.

The pathogenesis of retinal neovascularization is complex and its understanding remains incomplete. Current research focuses on the effects of hypoxia, inflammation and maturation in vascular diseases such as AMD.

This disease is marked by a decline in vision, image distortion, and the inability to read a word because of a scotoma. It is diagnosed in part by the formation of new blood vessels, which appear regardless of its form (atrophic or wet).

No current treatment for AMD, curative or preventive, is for the atrophic form. Over the recent years, anti-VEGF humanized monoclonal antibody therapy (bevacizumab (Avastin®) or ranibizumab (Lucentis®)) has already been widely used to prevent or inhibit neovascular form of AMDs and oedematous diabetic retinopathies. However, efficiency is limited to wet AMDs and this therapy has not yet been used to block the diverse pathological corneal neovascularizations. Moreover, as VEGF is not the only pro-angiogenic factor, resistances are to be expected.

Furthermore, many undesirable side effects appear during treatment, particularly with ranibizumab. The treatment with ranibizumab indeed induces conjunctival hemorrhage, pain in the eye, increased intraocular pressure, iris inflammation or uveitis, and blurred vision. Around 10% of wet AMD forms are not receptive (or only a little) to Avastin® or Lucentis® treatments. In order to obtain a stable result on the numerous patients afflicted with the wet AMD form, these patients may be treated with up to 24 Avastin® or Lucentis® intravitreal injections during 2 years, which increase the risk of deleterious events.

There is therefore a need for effective therapeutic agents in the treatment of neovascular eye diseases, with fewer side effects.

The invention therefore relates to the use of at least one anti-CD 160 antibody, preferably a compound selected from CL1-R2 monoclonal antibody (which may be obtained by the hybridoma CNCM 1-3204), its conservative fragments and its conservative derivatives, for the preparation of a drug for treating and/or preventing neovascular eye diseases.

The invention relates to at least one anti-CD 160 antibody, preferably at least one anti-CD 160 antibody which induces cell death of activated proliferating endothelial cells, for use for treating and/or preventing neovascular eye diseases.

The invention also concerns a compound selected from CL1-R2 monoclonal antibody (which may be obtained by the hybridoma CNCM 1-3204), its conservative fragments and its conservative derivatives, for use for treating and/or preventing neovascular eye diseases.

Preferably, said at least one anti-CD 160 antibody induces cell death of activated proliferating endothelial cells.

The invention also relates to an anti-CD 160 antibody and an anti-VEGF antibody as a combined preparation for simultaneous, separate or sequential use for treating and/or preventing neovascular eye diseases.

The combination of an anti-CD 160 antibody and an anti-VEGF antibody improves the chance of success of a therapeutic strategy for treating neovascular eye diseases since anti-CD 160 and anti-VEGF antibodies act on different targets and biological pathways.

The invention is also drawn to at least one anti-CD 160 antibody for use for treating and/or preventing neovascular eye diseases in a subject refractory to anti-VEGF treatment.

The present invention further relates to a method for treating a neovascular eye disease in a subject, preferably a human, in which a therapeutically effective amount an anti-CD 160 antibody, preferably CL1-R2, a conservative fragment thereof or a conservative derivative thereof, is administered to said subject.

The term "CD 160 antibody" or "anti-CD 160 antibody" refers to any antibody which binds to human CD 160. This term thus encompasses immunoglobulin molecules and immunologically active portions of immunoglobulin molecules directed against CD 160, i.e., molecules, including peptides, that contain an antigen binding site that immunospecifically binds to CD 160. As such, the term antibody refers not only to the whole antibody molecules, but also to antibody fragments as well as variants (including derivatives) of antibodies and antibody fragments. For fulfilling the purpose of the invention, several anti-CD 160 antibodies, directed against different epitopes of CD 160 may be used sequentially or simultaneously. The anti-CD 160 antibody according to the invention may be a compound selected from anti-CD 160 monoclonal antibodies, their conservative fragments and their conservative derivatives.

In the context of the present invention, said antibody does induce the cell death of activated proliferating endothelial cells and does not act directly on VEGF.

Said anti-CD 160 antibody may be chosen from CL1-R2, its conservative fragments and its conservative derivatives.

The CL1-R2 monoclonal antibody can be obtained from the hybridoma line deposited at the National Collection of Cultures of Microorganisms CNCM Institut Pasteur in accordance with the Budapest Treaty of Apr. 28, 2004 (Institute Pasteur CNCM, 25 rue du Docteur Roux F—75724 Paris Cedex 15, France). The deposited hybridoma has the deposit number CNCM 1-3204.

CD 160 belongs to family of immunoglobulins. The cDNA of human CD 160 corresponds to SEQ ID NO: 1 (1361 bp) described in WO 98/21240 (DANA-FARBER CANCER INSTITUTE).

The human CD 160 mRNA is available in GenBank under the accession number AF060981, the murine CD 160 mRNA is available in GenBank under the accession number AF060982.

The human CD 160 protein sequence corresponds to SEQ ID NO: 2 described in WO 98/21240, and is available under the accession number in Genbank AAC72302 (181 aa). CD 160 is a glycoprotein of 27 kDa, which is particularly present at the surface of endothelial cells.

The CL1-R2 target, i.e. the CD160 receptor, is expressed by activated proliferating endothelial cells, but not by quiescent endothelial cells. Activated proliferating endothelial cells are responsible for the formation of neovessels, and particularly the neovessels present in eye diseases.

CL1-R2 has a mechanism of action different from Avastin® or Lucentis®: it induces cell death of activated proliferating endothelial cells only, and does not act directly on VEGF. It also has a very high specificity for angiogenic neovessels. This antibody thus surprisingly offers a good therapeutic potential to patients refractory to anti-VEGF treatment. Therefore, the inventors met the burden to develop a highly promising strategy for treating neovascular eye diseases in a subject suffering from neovascular eye diseases which cannot be treated by anti-VEGF treatment.

The invention is thus also drawn to at least one anti-CD 160 antibody for use for treating and/or preventing neovascular eye diseases in a subject refractory to anti-VEGF treatment. Preferably, said anti-CD 160 antibody induces cell death of activated proliferating endothelial cells.

Preferably, said antibody is selected from CL1-R2 monoclonal antibody (which may be obtained by the hybridoma CNCM 1-3204), its conservative fragments and its conservative derivatives.

As used herein, the expression "subject refractory to anti-VEGF treatment" applies to a subject who is non responder to said anti-VEGF antibody. By "non responder", it is meant that subject does not recover, ameliorate, or stabilize his condition with anti-VEGF antibody. For example, a subject refractory to anti-VEGF treatment is a subject which has been unsuccessfully treated with anti-VEGF antibody or a subject known to be unable to successfully respond to a treatment based on anti-VEGF antibody. By providing a new strategy of treatment of a subject suffering from neovascular eye diseases and refractory to anti-VEGF treatment, the invention fulfills a long time felt need.

This antibody also may recognize an epitope, which is common among many species, like humans, rabbits, mice and macaque monkeys; this easily allows animal experimentations.

According to the invention CL1-R2 or a conservative fragment thereof or a conservative derivative thereof may be used to treat and/or prevent ocular neovascular diseases.

By "ocular neovascular diseases" or "neovascular eye disease", it is meant all neovascular eye diseases, comprising all neovascular diseases of the cornea, the retina and the choroid. These diseases comprise:

all forms of corneal neovascularizations whatever their causes might be, including the neovascularizations occurring as complications of corneal grafts and/or corneal infections or corneal environmental insults, including pathogen infections (like herpes) and chemical burns;

all forms of retinopathies, including diabetic ischemic and edematous forms, premature diabetic retinopathy, non proliferative and proliferative forms, macular cystoid edema, all forms of Age Related Macular Degenerations (AMD), all macular vitelliform degenerations, including Best disease, whenever they are associated with retinal and/or choroidal neovessels, ocular angiomas like Von Hippel-Lindau's disease; Eale's disease; Coats' disease;

Norrie disease (congenital exsudative vitreoretinopathy);

all forms of choroidal neovascularizations, retino-choroidal polypoidal vasculopathies whatever their clinical presentation might be, retrofoveolar choroidal neovessels associated with myopia, Sorsby's dystrophy which is nearly always associated with abnormal choroidal neovessels;

uveal melanomas, including choroidal melanomas and their metastases; and iridal rbeosis and neovascular glaucoma.

However, the scope of the neovascular eye diseases targeted by the CL1-R2 monoclonal antibody, its conservative fragments and its conservative derivatives may be wider.

Preferably, the ocular neovascular diseases (or neovascular eye diseases) are chosen from the group consisting of:

all forms of corneal neovascularizations, including the neovascularizations occurring as complications of corneal grafts and/or corneal infections and/or corneal environmental insults chosen from pathogen infections (like herpes) and chemical burns;

all forms of retinopathies, including diabetic ischemic and edematous forms, premature diabetic retinopathy, non proliferative and proliferative forms, macular cystoid edema, all forms of Age Related Macular Degenerations (AMD), all macular vitelliform degenerations, including Best disease; ocular angiomas like Von Hippel-Lindau's disease; Eale's disease; Coats' disease;

Norrie disease;

all forms of choroidal neovascularizations, retino-choroidal polypoidal vasculopathies, retrofoveolar choroidal neovessels associated with myopia, Sorsby's dystrophy;

uveal melanomas, including choroidal melanomas and their metastases; and iridal rbeosis and neovascular glaucoma.

Preferably, the invention relates to at least one anti-CD 160 antibody, preferably an antibody selected from CL1-R2 monoclonal antibody, its conservative fragments and its conservative derivatives, for treating and/or preventing all forms of Age Related Macular Degenerations (AMD).

By "preventing a disease", it is meant preventing the onset of the disease in a subject, particularly a human, in whom the disease has not yet declared.

By "treating a disease", it is meant decreasing the development of the disease or inhibiting the disease, i.e., stopping its development, regression or disappearance of symptoms and consequences of the disease, or the cessation of the causes of the disease.

According to the invention, the monoclonal antibody CL1-R2, but also its conservative derivatives and its conservative fragments, can be used to prevent and/or treat ocular neovascular diseases.

By "conservative fragments" and "conservative derivatives" of an anti-CD 160 antibody, it is respectively meant fragments and derivatives which retain the binding affinity and specificity of said antibody, preferably CL1-R2, for CD 160. Such conservative fragments and conservative derivatives are functional equivalents of said antibody, preferably CL1-R2. They are "conservative" because they bind at substantially the same epitope as said antibody, preferably CL1-R2 and/or can compete with said antibody, preferably CL1-R2, for binding to CD 160, and they retain the specificity of binding to CD 160. This specificity of binding is sufficient so that the conservative fragments or conservative derivatives do not bind to other HLA receptors than CD 160.

By "fragment" of an anti-CD 160 antibody, preferably CL1-R2, it is meant a portion of such an antibody, like a heavy chain, a light chain, a VL, a VH, a Fab, a Fab', a F(ab)2, F(ab')2, or dAb, but also any minimum unit consisting of amino acid residues that mimic the hypervariable region, such as a CDR (CDR1H, CDR2H, CDR3H, CDR1L, CDR2L, CDR3L). Fragments of an anti-CD 160 antibody of the invention, preferably CL1-R2, are conservative.

Only a portion of the antibody, i.e. the variable region, is involved in binding of the antibody to its epitope. The constant regions of antibodies activate the immune effectors, phagocytes or killer cells, as well as the complement, and these constant regions are not involved in binding to the antigen. An antibody with the constant region (Fc) enzymatically cleaved so as to preserve the hinge region is designated as a fragment F(ab')2 and retains the two binding sites to antigen.

Similarly, an antibody whose constant region, including the hinge region, has been enzymatically cleaved, or which has been produced without this region, is designated as a Fab fragment and retains only one of the two binding sites to antigen. Fab fragments consist of a light chain that is covalently linked to a portion of the heavy chain called Fd.

In the variable region, there are complementarity determining regions (CDRs, Complementary determining region) also known as hypervariable regions, which directly interact with antigen. Modifying the CDRs can thus help in changing the affinity of an antibody. In the variable region, there is a second type of regions called framework regions (FRs, frameworks), which maintain the tertiary structure of the CDRs. These framework regions are quite specific of the specie in which the antibody was produced. In the Fd fragment of heavy chain and light chain, there are four framework regions (FR1-4) respectively separated by three CDRs (CDR 1 to 3).

The conservative fragments of the invention also comprise dAbs. dAbs (single domain antibodies) are antibodies which comprise only one protein chain which derives from one of the two domains of the normal structure of an antibody. Indeed, in certain cases, half of an antibody can bind its target antigen with an affinity comparable to the affinity of the wild-type antibody.

The conservative fragments of an anti-CD 160 antibody, preferably CL1-R2, according to the invention can be produced using methods well known in the prior art. Such fragments can be obtained by routine methods, such as a proteolytic digestion (for example, pepsin digestion to generate F(ab')2; digestion with papain to generate Fab).

Preferably, the conservative fragments of CL1-R2 are selected from Fab, Fab', F(ab)2, F(ab')2 and dAb of CL1-R2.

By "conservative derivative" of CL1-R2, it is meant a fragment of CL1-R2, preferably including at least one CDR of CL1-R2, preferably at least one CDR3 of CL1-R2, fused to at least one sequence different from the natural sequence (e.g. a linker sequence of another species . . . ), said derivative having binding affinity to CD 160 comparable to that of CL1-R2, and a CD160-binding specificity similar to that of CL1-R2.

The conservative derivatives can be obtained according to general knowledge of the person skilled in the art, by synthesis and/or genetic engineering.

A conservative derivative of the invention may be monovalent (a single binding site CD 160), or multivalent (at least two binding sites to CD 160). Preferred conservative multivalent derivatives include derivatives tetravalent conservative.

The conservative derivatives include chimeric antibodies that can be obtained by grafting at least one Fv fragment of CL1-R2 to a Fc fragment derived from another antibody. The Fc fragment is preferably chosen to be as less immunoreactive as possible for the subject to which it is administered. For example, when the antibody is intended to be administered to a human being, said Fc fragment is preferably a human Fc fragment.

The conservative derivatives of the invention also include humanized antibodies that can be obtained by grafting at least one CL1-R2 or a portion thereof on a human framework fragment (hFR). Once again, the objective is to obtain the antibodies as less immunogenic as possible for the body to which it is administered.

The conservative derivatives of the invention also include single chain variable fragments Fv: they are called scFv. A single chain variable fragment scFv is a fusion protein comprising the variable regions of light chain VL and heavy chain VH, connected by a short linker of about 25 amino acids. The appropriate linkers are those which allow the VH and VL domains to be structurally conformed in the same way as the original structure of the whole antibody CL1-R2, and thus to maintain the binding specificity. Such linkers are known to those skilled in the art, for example in application WO 88/01649 (GENEX Corp.). The scFv can be monovalent or multivalent.

The conservative derivatives of the invention also include (scFv)2, which are dimers of scFv.

The conservative derivatives of the invention also include bispecific antibodies. Bispecific antibodies comprise two binding sites for two different antigens. They comprise at least the VH and VL domains for one antigen, and the VH and VL domains for another antigen. Preferably, bispecific antibodies according to the invention comprise one binding site to CD 160, and one binding site to VEGF.

The conservative derivatives of the invention also include diabodies.

Diabodies are a new class of small bivalent and bispecific antibody fragments. They comprise a VH domain connected to a VL domain on the same polypeptide chain (VH-VL) connected by a peptide linker that is too short to allow pairing between the two domains on the same chain. This forces pairing with the complementary domains of another chain and promotes the assembly of a dimeric molecule with two functional antigen binding sites.

To construct bispecific diabodies the V-domains of antibody A and antibody B are fused to create the two chains VHA-VLB, VHB-VLA. Each chain is inactive in binding to antigen, but recreates the functional antigen binding sites of antibodies A and B on pairing with the other chain.

For example, a conservative derivative of CL1-R2 includes a scFv comprising at least one VH region of CL1-R2 linked to at least one VL region of CL1-R2 by a peptide linker L; the scFv may have a specific VL-L-VH or VH-VL-L orientation.

Another conservative derivative of CL1-R2 comprises a scFv multimer derived from CL1-R2 fused to an Fc fragment.

Another conservative derivative of CL1-R2 is obtained by adding one or more Fab derivative(s) of CL1-R2 at the C-terminus of each heavy chain H of a whole CL1-R2.

Another conservative derivative of CL1-R2 is obtained by covalently linking whole CL1-R2 antibodies together to achieve an aggregated form.

Another conservative derivative of CL1-R2 is obtained by linking two or more Fabs in head-to-tail.

A multivalent scFv of the invention can be obtained by linking at least two scFv together (for example (scFv)2). The association may be covalent or non covalent. As examples, mention may be made of scFv tetramers (4-binding sites CD 160). The interest of a multivalent scFv is the presence of several binding sites to CD 160, which increases the ability to bind to the antigen.

The multimeric scFv may be monospecific, i.e. all their binding sites target CD 160.

Alternatively, the multimeric scFv can comprise one or more binding site(s) to CD 160, and one or more binding site(s) to another antigen from CD 160. For example, such an antigen may be VEGF.

The methods for producing multimeric scFv are known in the prior art, for example WO 94/13806 (The Dow Chemical Company) or WO 93/11161 (Enzon Inc.).

Preferably, conservative derivative of CL1-R2 according to the invention are selected from the scFv, the (scFv)2, the diabodies, the multimeric scFv derived from CL1-R2 and fused to a Fc fragment, the whole CL1-R2 antibodies linked together to achieve an aggregated form, and the antibody forms comprising at least two Fabs bound face-to-tail.

CL1-R2 antibody, one of its conservative fragments or one of its conservative derivatives, may be present in a pharmaceutical composition or drug. This pharmaceutical composition comprises preferably a pharmaceutically acceptable vehicle. The term "pharmaceutically acceptable" refers to a nontoxic material that is compatible with a biological system such as a cell, cell culture, tissue or organism, and that does not interfere with the effectiveness of the biological activity of other active ingredients of the composition. Vehicle characteristics depend on the mode of administration.

The pharmaceutical composition or drug can be in any form administrable to a patient, and includes solutions, suspensions, lyophilized powders, capsules and tablets.

The pharmaceutical composition or drug can be presented in a form consistent with an injection, i.e. a local injection, an administration through the mucosa, an inhalation, an oral administration and, more generally, any formulation suitable for the intended purpose. Preferably, the pharmaceutical composition or drug is presented in a form consistent with a sub-conjunctival, sub-tenonal, intra-vitreal, sub-retinal, intra-orbital, intraveinous, intramuscular, subcutaneous or intraocular administration.

The present invention further relates to a method for treating a neovascular eye disease in a subject, preferably a human, in which a therapeutically effective amount of CL1-R2, a conservative fragment thereof or a conservative derivative thereof, is administered to the subject. The CL1-R2 antibody, its conservative fragments or its conservative derivatives, is administered in a therapeutically effective amount. A therapeutically effective amount represents an amount sufficient to prevent and/or treat the targeted neovascular eye disease. This amount can vary with age, sex of the subject and the stage of the disease and will be determined by the skilled person. A therapeutically effective amount may vary between 0.01 mg/kg and 50 mg/kg, preferably between 0.1 mg/kg and 20 mg/kg and more preferably between 0.1 mg/kg and 2 mg/kg, preferably in one administration per month.

The mode of administration may be by injection or by gradual infusion. The injection is preferably intravitreal.

Preparations for intravitreal administration may include aqueous or nonaqueous sterile suspensions or emulsions. Examples of nonaqueous solvents are propylene glycol, polyethylene glycol, vegetable oils such as olive oil or injectable organic esters such as ethyl oleate. Aqueous vehicles include water, alcohol/water solutions, emulsions or suspensions.

CL1-R2, one of its conservative fragments or one of its conservative derivatives of the invention may also include another component. For example, CL1-R2, conservative fragments thereof or conservative derivatives thereof can be labelled. Examples of markers include enzymes, radioisotopes, fluorescent compounds, colloidal metals, chemiluminescent compounds and bioluminescent compounds. Methods for binding a marker to an antibody are well known to those skilled in the art.

Another labeling technique consists in coupling the antibodies to haptens of low molecular weight; these haptens can be specifically modified by a second reaction. Examples of haptens are biotin, which reacts with avidin, or dinitrophenol, pyridoxal, or fluorescein, which can react with specific anti-haptens.

In a preferred embodiment, antibodies of the invention may be labelled with a detectable molecule or substance, such as a fluorescent molecule, a radioactive molecule or any others labels known in the art. Labels are known in the art that generally provide for (either directly or indirectly) a signal.

As used herein, the term "labelled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibodies of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

Results obtained in several groups of rabbits which were administrated with:

IgG1 alone (injections of 25 µg);
Avastin® alone (two injections of 25 µg);
CL1-R2 alone (2 injections of 25, 50 or 100 µg);
Avastin® combined with IgG1; and
Avastin® combined with CL1-R2.
Grade corresponds to the length of the neovessels.

Figure 5:
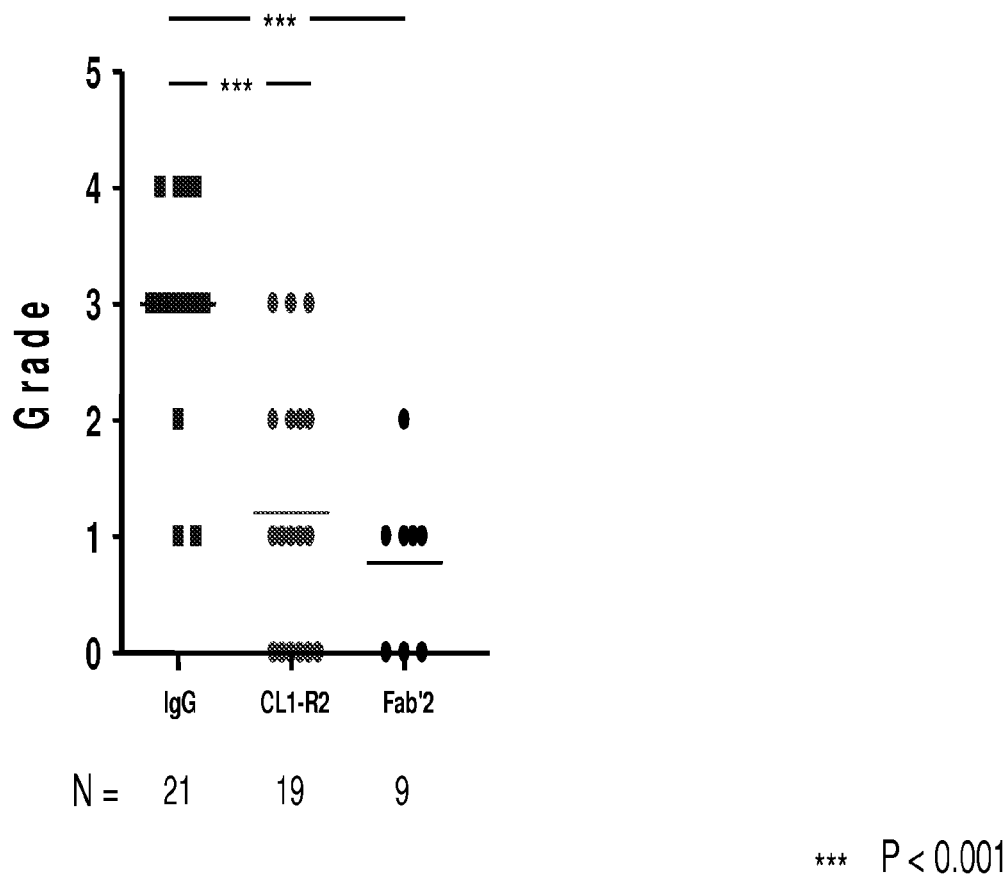

FIG. 5: Effect of CL1-R2 in complete form et CL1-R2 in Fab'2 form.

The figure shows the effect of CL1-R2 in complete form, the effects of CL1-R2 in Fab'2 form on corneal neovascularization, and those provided by a control IgG1.

Grade corresponds to the length of the neovessels.

Figure 6:
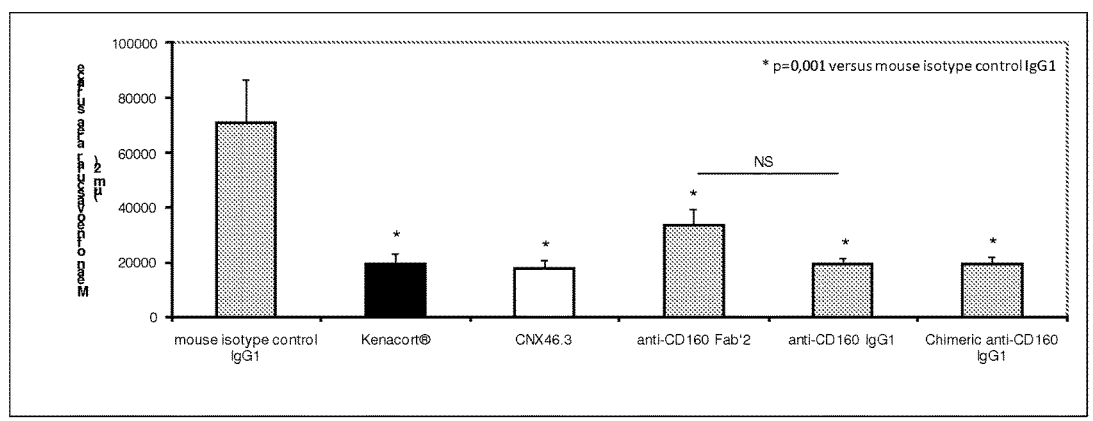

FIG. 6: Effects of mouse and chimeric anti-CD 160 mAb in a mouse model of AMD (laser-induced CNV)

Results obtained in several groups of mice which were administrated with:

mouse IgG1 isotype control;
Kenacort retard 40®;
CNX46.3 (rat anti-mouse CD 160 mAb from eBioscience);
mouse anti-human CD160 Fab'2;
mouse anti-human CD 160 IgG1; and
chimeric anti-human CD 160 IgG1.
The average of neovascular area surface is measured.

EXAMPLE 1

Material and Methods

Murine anti-CD 160 CL1-R2 mAb. The mouse anti-CD 160 CL1-R2 mAb (IgG1) was developed in our laboratory and was evaluated as an anti-CD 160 mAb during the 7th Human Leukocyte Differentiation Antigen Workshop (26). We produced the CL1-R2 mAb from a specific secreting hybridoma cell line by using the high cell density system CeLLine (VALDEA Biosciences). The mouse IgG1 isotype control monoclonal antibody He6 was developed by immunizing mice with hepatitis B surface antigen (HBs). Both CL1-R2 and IgG1 isotype control were similarly purified by affinity chromatography on a HiTrap™ protein G column (GE Healthcare) in an ÄKTA™ purifier system, dialyzed against PBS pH 7.0, concentrated and filtered through 0.22-µm filters.

Animals. We used BALB/c, C57BL/6J and NMRI-nu (nu/nu) Nude mice (Janvier Laboratories). Mice were 7-10 weeks old except for those used for the ischemic retinopathy experiments, which were seven days old. Animals were housed in a conventional temperature controlled room (21° C.), exposed to a daily 12-hour period of light and dark and fed ad libitum with a balanced diet as determined by the Jackson laboratory for the C57BL6/J mouse strain. We used male New Zealand albino rabbits from Institut National de la Recherche Agronomique (Castanet-Tolosan). For the mouse retina experiments, animals were handled according to the guidelines of the institutional animal care committee, using protocols approved by the Ethics Committee and the ARVO Statement for use of Animals in Ophthalmic and Vision Research. All other animal experiments were carried out in agreement with the European Union guidelines and approved by the local ethic committee (Midi-Pyrenees, France).

In vivo rabbit corneal angiogenesis assay. The corneal pocket assay used in this study has been previously described (28). We made an incision in the upper side of the cornea, 2 mm from the limbus in anesthetized rabbits. FGF2-treated implants (500 ng, R&D Systems) were inserted into this pocket. Subconjunctival injections of CL1-R2 mAb or control IgG1 (100 µg in 30 µl PBS) were administered to the upper side of the limbus 24 and 72 hours after corneal implantation. Corneal neovascularization was measured 8 days after implantation and was scored on a four-grade scale based on the length of the newly formed vessels from the limbus to the FGF2-containing implant (28).

Murine model of oxygen-induced retinopathy and intravitreal injections. Retinal neovascularization was induced in mouse C57BL/6J pups using a well-established and reproducible model of oxygen-induced retinopathy (32). Briefly, mice (7-day old, P7) and their nursing mothers were placed in an airtight incubator and exposed to a 75±2% oxygen atmosphere for 5 days. The oxygen level was continuously monitored with a PROOX oxygen analyzer (model 110, BioSpherix). Mice were removed on P12 and maintained in normoxic conditions (room air) until P17. Mice were injected intravitreally under an operating microscope. With the exception of the non-injected group, each pup received an intravitreal injection in their left and right eyes on P12. Briefly, mouse pups were anesthetized with an intramuscular injection of ketamine (100 mg/kg body weight) and xylazine (10 mg/kg body weight). The palpebral fissures were opened with microscissors and pupils were dilated with topical 10% phenylephrine and 0.5% tropicamide. The tip of a 10-mm 33-gauge steel needle, mounted on a 5 µl Hamilton syringe was pushed through the sclera, 1 mm posterior to the corneoscleral limbus, into the vitreous body. Approximately 1 µl of CL1-R2 mAb (5 µg/µl), bevacizumab (25 µg/µl, Roche) or IgG1 isotype control mAb (5 µg/µl) was injected into the vitreous cavity.

Qualitative and quantitative assessment of retinal neovascularization. Mice were killed at P17 to analyze neovascularization by histology and quantitative measurements. Some mice underwent retinal angiography with fluorescein-dextran. For this qualitative assessment, we anesthetized mouse pups as previously described and perfused the heart through the left ventricle with 1 ml of PBS containing 50 mg/ml fluorescein-labeled dextran (2×106 average molecular weight, Sigma) that had been cleared by centrifugation for 5 min at 10,000 rpm. The eyes were enucleated and fixed in 4% paraformaldehyde for 3 hours. The cornea and lens were removed and the retina was dissected from the eyecup. The retina was cut into four quadrants and flat-mounted in Vectashield under a coverslip for examination by fluorescence microscopy. At least 12 eyes from each treatment were examined. For the histological analysis, mouse pups were killed, their eyes enucleated, fixed in 4% paraformaldehyde for at least 16 hours at 4° C. and embedded in paraffin. We prepared sagittal 5-µm sections with the HM355, MICROM MICROTEC microtome, stained sections with periodic acid-Schiff reagent and counterstained with H & E. We counted 5-8 sections on each side of the optic nerve. Two trained investigators counted blindly the number of neovascular endothelial cells and vessel lumens across the entire retinal sample in each intact section at ×100 magnification. Average numbers of endothelial cell nuclei and vessel numbers were determined using a Poisson regression model for clustered data; 95% confidence intervals of the average number estimates are figured as error bars. P values were corrected for post-hoc group comparisons by the Bonferroni method.

Statistics. For the mouse and rabbit model experiments, quantitative data (presented as mean±SEM) were analyzed with the GraphPad Prism 4 or Prism 5 programs. A mean value for each vascular variable (intravital microscopy and histological analysis) was determined for each animal, and these values were used to calculate the overall mean for all the animals in each experimental group. Before carrying out statistical tests, we determined whether the data were normally distributed and evaluated their variance. We then carried out appropriate tests as indicated. For in vivo time-course experiments, we used two-way ANOVA analysis or Student's t-test. We report the actual P value for each test. P<0.05 was considered statistically significant. For the retina counts, because there are two nested levels of dependence between histological sections pertaining to the same eye and the same mouse, counts of cell nuclei and vessel lumens were analyzed by a Poisson generalized linear mixed model (59) with proc GLIMMIX of the SAS statistical package v9.1.3 (Sas Institute). We considered experimental treatment groups as fixed effect factors and individual eyes as random effects. At the upper limit, robust empirical variance of the fixed effect estimates (60) was computed by defining the mice as clusters. P<0.05 was considered statistically significant.

Results

Figure 1:
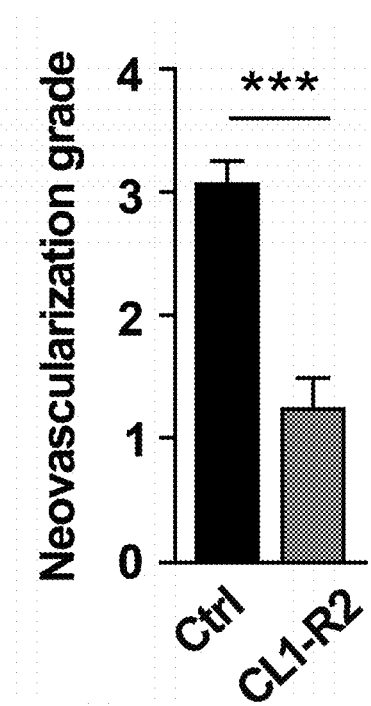
FIG. 1: CL1-R2 inhibits FGF2-induced rabbit corneal neoangiogenesis. Quantitative analysis of neovascularization in control IgG1 (Ctrl)– and CL1-R2-treated corneas. Values are means±SEM obtained from four separate experiments, n=5 rabbits per group for each experiment experiment. ***P<0.0001 (Mann-Whitney test). Neovascularization was assessed 8 days after corneal grafting of FGF2-containing implants. Subconjunctival injections of CL1-R2 or IgG1 Ctrl were performed 24 and 72 h after implantation and was scored an a 4-grade scale based on the length of the newly-formed vessels from the limbus to the FGF2-containing implants.
Figure 2A:
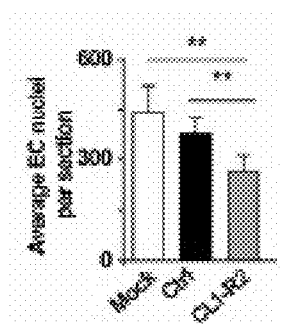
FIG. 2A: CL1-R2 reduces retinal neovascularization in a murine model of oxygen-induced retinopathy. Quantitative assessment of the retinal vascularization (histology, retinal section counts) from mice exposed to hyperoxic conditions without injection ("Mock", n=6) or injected intravitreally with control IgG1 (Ctrl, 5 µg, n=9), or CL1-R2 (5 µg, n=11). Average number of endothelial cell (EC) nuclei **$P<0.001$.
Figure 2B:
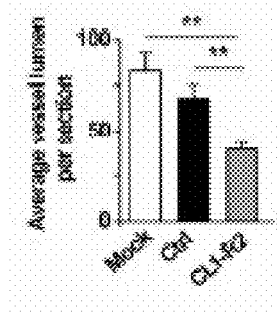
FIG. 2B: CL1-R2 reduces retinal neovascularization in a murine model of oxygen-induced retinopathy. Quantitative assessment of the retinal vascularization (histology, retinal section counts) from mice exposed to hyperoxic conditions without injection ("Mock", n=6) or injected intravitreally with control IgG1 (Ctrl, 5 µg, n=9), or CL1-R2 (5 n=11). Average number of vessel lumen. **$P<0.001$.
Figure 3A:
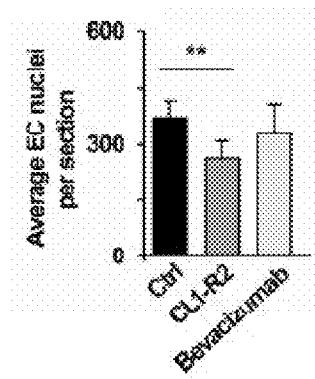
FIG. 3A: Quantitative assessment of retinal vascularisation. The average numbers of endothelial cell nuclei were determined using a Poisson regression model for clustered data. 95% confidence intervals of the average number estimates are shown as error bars. P values were corrected post-hoc group comparisons by the Bonferroni method. *$P<0.05$, **$P<0.001$.
Figure 3B:
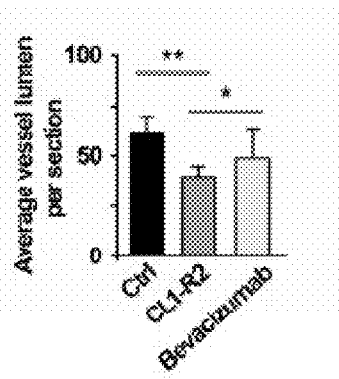
FIG. 3B: Quantitative assessment of retinal vascularisation. The average numbers of vessel lumens were determined using a Poisson regression model for clustered data. 95% confidence intervals of the average number estimates are shown as error bars. P values were corrected post-hoc group comparisons by the Bonferroni method. *$P<0.05$, **$P<0.001$.

The CL1-R2 mAb inhibits ocular neovascularization in rabbit cornea and oxygen-induced retinopathy in a mouse model. The anti-angiogenic properties of CL1-R2 mAb was evaluated in vivo by using two different ocular neoangiogenesis animal models. The vertebrate eye has an advantage for these studies in that it is considered to be an immuno-privileged site (31), thus possibly devoid of immune cells that could bind CL1-R2. We first used a rabbit corneal pocket assay (28) to determine whether CL1-R2 inhibits fibroblast growth factor 2 (FGF2)-induced corneal neovascularization. The cornea is normally devoid of both blood and lymphatic vessels and actively maintain this avascularity (31). In this model, neovessels are attracted from the limbus. Neovascularization was assessed eight days after transplantation of corneal implants containing FGF2 and two subconjunctival injections of 100 µg of CL1-R2 or control IgG1. Treatment with CL1-R2 significantly decreased corneal neovascularization when compared with control IgG1-treated rabbits (FIG. 1). These findings indicate that CL1-R2 treatment inhibits growth factor-induced corneal neovascularization. Next, the effect of CL1-R2 was investigated in a mouse model of human retinopathy of prematurity by exposing premature newborn mice (P7-P12) to high oxygen levels (32, 33). In 100% of these animals the return to normoxic conditions induced retinal ischemia and VEGF dependent preretinal vascularization (32). A qualitative assessment of the retinal vasculature was first performed on flat-mounted FITC-dextran-perfused whole retinas after intravitreal injections of CL1-R2 or control IgG1 (data not shown). Retinas from normal untreated animals exhibited normal vascularization i.e. both superficial and deep vascular layers that extended from the optic nerve to the periphery. The vessels formed a radial branching pattern in the superficial retinal layer and a polygonal reticular pattern in the deep retinal layer. Retinas from oxygen-treated animals with no intraocular injection ('Mock') or intraocular injection of control IgG1 ('Ctrl') displayed neovascular tufts that released fluorescein and had tortuous radial vessels and a central avascular zone, consistent with previous descriptions of this model (32, 33). After intraocular injection of CL1-R2, avascular areas dramatically decreased in size and the retinas contained fewer neovascular tufts and fewer tortuous and dilated radial vessels (data not shown), suggesting better perfusion efficiency in the central vessels. Eyes from the various untreated or oxygen-treated animals were analyzed further by histology. Serial ocular tissue sections were stained with periodic acid-Schiff reagent to visualize the nuclei of endothelial cells (data not shown). Unlike the retinas from mice in a normoxic environment (Normal retina), the retinas of mock-treated mice typically contained abundant longitudinal and transverse aberrant microvessels of various sizes in the vitreous space and inner retina, as well as endothelial cell nuclei. Retinas from control IgG-treated animals displayed similar neovascularization with abundant aberrant microvessels and endothelial cell nuclei. By contrast, retinas from mice injected with CL1-R2 had significantly fewer aberrant vessels, which were greatly reduced in size, especially in the vitreous space and within the retina, and fewer endothelial cell nuclei. To quantify retinal neovascularization, endothelial cell nuclei and lumens of neovessels were counted in a large number of samples before and after the administration of antiangiogenic or control treatments (FIGS. 2, A and B). These are crucial parameters for evaluating accurately any retinal antiangiogenic effect. Intravitreal injection of CL1-R2 significantly decreased the mean number of endothelial cell nuclei per section in both ganglion cell and inner nuclear layers as compared to animals injected with control IgG1 (P<0.001; FIG. 2A). Furthermore, intraocular injection of CL1-R2 reduced the average number of vessel lumens per section by ~50% and ~35% when compared with mock-treated (P<0.001) or IgG1-treated control mice (P<0.001), respectively (FIG. 2B). The effect of CL1-R2 treatment was then compared to that of the widely used mAb bevacizumab in the same mouse model regardless of the controversy regarding the specificity of bevacizumab to neutralize murine VEGF-A (34). Several reports have indeed conclusively demonstrated that bevacizumab, despite its weak affinity for the VEGF-A produced by mice, rats, guinea-pigs and rabbits, is efficient in treating experimentally induced corneal neovascularization in these animals (35-39). Furthermore, a recent study showed unambiguously that bevacizumab had a very significant inhibitory effect on retinal angiogenesis in the oxygen-induced retinopathy mouse model (40). These latter results are in full agreement with ours. After intraocular injection of bevacizumab, normalized retinal vascularization was observed on flat-mounted retinas comparable to that obtained after CL1-R2 treatment (data not shown). Quantitative analysis indicated that the average number of vessel lumens per section was lower in bevacizumab injected-mice than in IgG1-treated control mice and there was no significant difference between CL1-R2-treated and bevacizumab-treated mice (FIG. 3, P=0.93). Overall, these data show that CL1-R2 mAb monotherapy efficiently suppresses pathological angiogenesis in rabbit cornea and mice with a retinopathy model of prematurity.

EXAMPLE 2: SYNERGISTIC EFFECT OF CL1R2 AND ANTI-VEGF ANTIBODY ON INHIBITION OF NEOVASCULARIZATION

The inventors evaluated the anti-angiogenic properties of CL1-R2 mAb in vivo in combination with an anti-VEGF antibody (Avastin®) by using corneal neoangiogenesis models with FGF2-treated implants as in Example 1.

For this purpose, they compared the results obtained in several groups of rabbits which were administrated with:
IgG1 alone (injections of 25 µg);
Avastin® alone (two injections of 25 µg);
CL1-R2 alone (2 injections of 25, 50 or 100 µg);
Avastin® combined with IgG1; and
Avastin® combined with CL1-R2.

Each group comprises 4 rabbits. Grade corresponds to the length of the neovessels.

Figure 4:
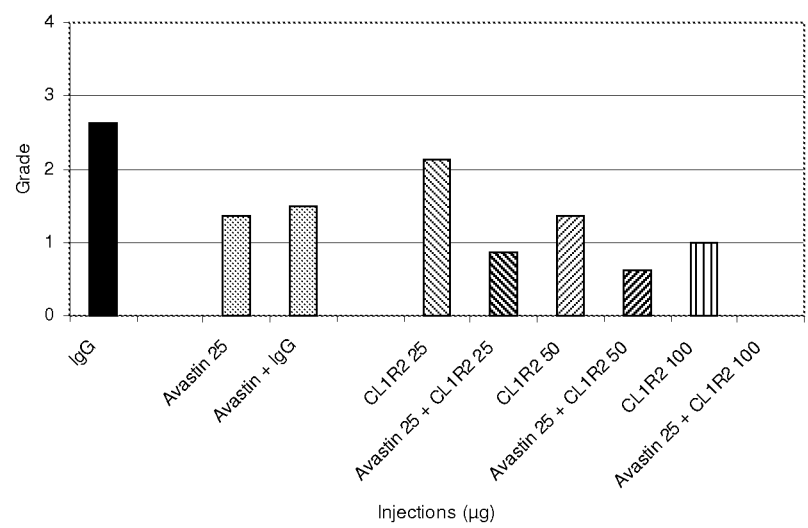
FIG. 4: Synergistic effect of CL1R2 and anti-VEGF antibody on inhibition of neovascularization.

The results are shown on FIG. 4. The inventors evidenced that use of CL1-R2 along with an anti-VEGF antibody provides better results in the inhibition of neovascularization in an ocular neoangiogenesis model.

This result indicates that CL1-R2 and anti-VEGF are highly useful in combination for treating neovascular eye diseases, since their combination provides a synergistic inhibition of neovascularization.

EXAMPLE 3: EFFECT OF CL1-R2 IN COMPLETE FORM ET CL1-R2 IN FAB'2 FORM

The inventors compared the effects of CL1-R2 in complete form and the effects of CL1-R2 in Fab'2 form on corneal neovascularization. For this purpose they used a control IgG1.

The results are disclosed on FIG. 5. Grade corresponds to the length of the neovessels. The inventors have shown that CL1-R2 in complete form provides better results on inhibition of neovascularization compared to the effect provided by the control IgG1.

They further evidenced that Fab'2 form is highly adapted for inhibition neovascularization, since it provide better results compared to CL1-R2 in complete form and control IgG1.

EXAMPLE 4: EFFECTS OF MOUSE AND CHIMERIC ANTI-CD 160 MAB IN A MOUSE MODEL OF AMD

The aim of this study was to assess the therapeutic efficacy of both mouse and chimeric anti-CD160 mAb for inhibiting pathological ocular neovascularization in a mouse model of choroidal neovascularization (CNV) reproducing many features of AMD. Choroidal neoangiogenesis was induced by krypton laser impacts administration. CNV was assessed qualitatively by in vivo angiography, and quantitatively by direct measurements of the area of CNV on flat-mounted choroids.

Materials and Methods

Animals

Male C57Bl/6J mice (6 weeks old) were obtained from Janvier Laboratories (Lassalle, QC). Animals were housed in a conventional controlled-temperature room (21° C.), with a daily 12 h light period. They were fed ad libitum with a balanced diet for the C57BL6/J mouse strain recommended by Jackson Laboratories. Animals were handled in accordance with the guidelines of the institutional animal care committee, using protocols approved by the institutional review board, and in accordance with the ARVO Statement for the Use of Animals in Ophthalmic and Vision Research. The general state of the mice, including their body weight, food intake and behavior, was monitored throughout the in vivo experiment.

Murine Model of Laser-Induced CNV

CNV was generated by the krypton laser-induced rupture of Bruch's membrane, as previously described (Tobe et al., 1998, Edelman Jl 2000; Montezuma S R et al 2009). Mice were anesthetized by intramuscular injection of a mixture of 100 mg/kg ketamine (Ketamine 1000®, Virbac France, Carros, France) and 10 mg/kg xylazine (Rompun 2%®, Bayer Pharma, Puteaux, France). Mouse corneas were anesthetized with 0.4% oxybuprocaine hydrochloride (Cebesine®, Chauvin Laboratory, Montpellier, France) and pupils were dilated with 10% phenylephrine (Neosynephrine Faure 10%®, Pharmaster, Erstein, France) and 0.5% tropicamide (Mydriaticum®, Farmila, Thea Farmaceutici, Settimo Milanese, Italy) eye drops.

Three laser-induced impacts were induced in one eye per mouse (usually at the 9, 12 and 3 o'clock positions around the optic disc), with a krypton laser carefully calibrated for creating disruptions of Bruch's membrane and secondary choroidal neovascularization sprouting from the choriocapillaris (spot size 50 µm; power 400 mW, exposure time 100 ms, Ophthalas, Biophysics Medical, Clermont Ferrand, France) and a contact lens. In all treated eyes included in the study, a reactive, traumatic bubble was observed at the retinal surface after laser treatment, providing evidence of appropriate focusing and as an indication for the rupture of Bruch's membrane.

Intravitreal Injection Protocol

All procedures were performed under an operating microscope and, each animal received an intravitreal injection into the eye one day after the krypton laser administration.

The mice (6 weeks old) were assigned to 6 groups:
Group 1: chimeric anti-human-CD160 mAb-treated mice (CL1-R2 chim., n=15);
Group 2: mouse anti-human-CD 160 mAb-treated mice (CL1-R2, n=17);
Group 3: mouse IgG1 isotype control mAb-treated mice (HE6, n=15);
Group 4: rat anti-mouse CD160 mAb-treated mice (CNX46-3, n=14);

Group 5: Fab'2 fragment of mouse anti-human-CD 160 mAb-treated mice (Fab'2, n=15);

Group 6: Kenacort retard 40®-treated mice (Kenacort, n=15).

Mice were anesthetized by intramuscular injection of a mixture of ketamine (100 mg/k) and xylazine (10 mg/kg). The pupils were dilated with topical 10% phenylephrine and 0.5% tropicamide. The tip of a 10 mm 33 gauge-steel needle mounted on a 5 µl Hamilton syringe was pushed through the sclera to a position 1 mm posterior to the corneoscleral limbus, in the vitreous body. For each product, 1 µl was injected into the vitreous cavity:
- chimeric anti-human-CD 160 mAb (10 µg/µl, batch 29120-00, MAT biopharma),
- mouse anti-human-CD 160 mAb (10 µg/µl, batch 280910-00, MAT Biopharma),
- mouse IgG1 isotype control mAb (10 µg/µl, batch 191110-00, MAT Biopharma),
- rat anti-mouse CD160 mAb (10 µg/µl, eBioscience),
- Fab'2 fragment of mouse anti-human-CD160 mAb (10 µg/µl, batch 191110-00, MAT Biopharma)
- Kenacort retard 40® (40 mg/ml, Bristol Myers Squibb, France).

Qualitative and Quantitative Assessment of CNV

Fourteen and twenty-one days after krypton laser administration, mice underwent fluorescein angiography for the qualitative assessment of choroidal neovascularization. Mice were sacrificed 21 days after krypton laser administration, for quantitative analysis of choroidal flat-mounts.

Angiography in vivo—Fluorescein angiography was performed fourteen and twenty-one days after the induction of laser-induced impacts. Mice were anesthetized as previously described and serial fundus photographs (Canon CF-60UVi, Haag-Streit, Chambery, France) were taken after the intraperitoneal injection of 0.5 ml of 10% fluorescein sodium (10% Faure®, Novartis Pharma, Rueil-Malmaison, France). Fluorescein leakage from newly formed abnormally permeable vessels led to the development of hyperfluorescent spots at the sites of the krypton laser impacts induced-lesions, clearly distinguished from the normal retinal and choroidal vasculatures.

Choroidal flat-mounts—Twenty-one days after laser treatment, cardiac perfusion was performed through the left ventricle, with 300 µl of a 50 mg/ml solution of fluorescein-labeled dextran in PBS (fluorescein isothiocyanate-dextran, $2 \times 10^6$ mean molecular weight, Sigma, France), clarified by centrifugation for 5 minutes at 10000 rpm (1110×g). The laser-treated eyes were enucleated and immediately fixed by incubation in 4% paraformaldehyde for at least 16 hours at 4° C. The cornea and lens were removed and the entire retina was carefully dissected from the eyecup. The retinal pigment epithelium-choroid-sclera eyecups were dissected through four to five radial incisions, flat-mounted on a slide in Vectashield and covered with a coverslip for fluorescence microscopy with a ×10 objective (Axioplan 2, Zeiss, Le Pecq, France). A calibrated image was also obtained. The area affected by choroidal neovascularization (in $\mu m^2$) was measured with Image J Software. The measurements of the neovascular area obtained for multiple lesions were averaged for individual eyes and individual animals.

Statistical Analysis

Data are presented as means±standard error. Statistical analysis was carried out using parametric tests (analysis of variance ANOVA, and PLSD Fisher test—Statview Software, version 5) for the detection of significant differences between groups. Values of P<0.05 were considered statistically significant.

Results

Mortality rates were similar in the groups during the experiment: 3/17 (5.8%) in group 2, 2/15 (13%) in group 3, 1/14 (7.1%) in group 4, 2/15 (13.3%) in group 5, and no death in groups 1 and 6. The deaths occurred during or after anesthesia for laser photocoagulation or angiography in vivo.

No significant difference in body weight gain was subsequently observed between the mice of the 6 groups.

The efficiency of the treatment was quantified by directly measuring the area displaying choroidal neovascularization on flat-mounted choroids, as previously described (Edelman and Castro, 2000).

The analysis of the area displaying CNV was performed using parametric tests (analysis of variance ANOVA and PLSD Fisher test). Results are shown in FIG. 6. CNV areas were significantly smaller in the CL1-R2 (group 2, P<0.0001) and Fab'2-treated mice (group 5, P=0.0001) than in mouse IgG1 isotype control-treated mice (group 3). Kenacort® (group 6, P<0.0001) treatments, used as positive control, and CNX46-3 (group 4, P<0.0001), displayed similar effects in comparison with isotype control group. Treatment with CL1-R2 chimeric antibody significantly decreased the CNV areas in comparison with those measured in mouse IgG1 isotype-treated mice (P<0.0001). It is worth to notice that a similar effect was observed between CL1-R2 and CL1-R2 chimeric treatments (P=0.9888) and between Fab'2 and CL1-R2 or CL1-R2 chimeric treatments (P=0.0951 and P=0.0925, respectively).

Quantitative assessments of neovascularization suggested that CL1-R2, CL1-R2 chimeric, Fab'2 treatments and CNX46-3 i) decreased the area affected by CNV in comparison with mouse IgG1 isotype control treatment and ii) prevented choroidal neovascularisation, in a well established mouse model of krypton laser-induced CNV and as well as the positive control (Kenacort®).

REFERENCES

In this application, the references cited are:
1. Carmeliet P. Angiogenesis in life, disease and medicine. Nature. 2005; 438(7070):932-936.
2. Sherris D. Ocular drug development-future directions. Angiogenesis. 2007; 10(2):71-76.
3. Buckanovich R J, et al. Endothelin B receptor mediates the endothelial barrier to T cell homing to tumors and disables immune therapy. Nat Med. 2008; 14(1):28-36.
4. Shojaei F, Ferrara N. Antiangiogenesis to treat cancer and intraocular neovascular disorders. Lab Invest. 2007; 87(3):227-230.
5. Cao Y. Tumor angiogenesis and molecular targets for therapy. Front Biosci. 2009; 14(3962-3973.
6. Folkman J. Angiogenesis: an organizing principle for drug discovery? Nat Rev Drug Discov. 2007; 6(4):273-286.
7. Paez-Ribes M, et al. Antiangiogenic therapy elicits malignant progression of tumors to increased local invasion and distant metastasis. Cancer Cell. 2009; 15(3):220-231.
8. Takeda A, et al. CCR3 is a target for age-related macular degeneration diagnosis and therapy. Nature. 2009; 460 (7252):225-230.
9. Ma W W, A djei A A. Novel agents on the horizon for cancer therapy. CA Cancer J Clin. 2009; 59(2): 111-137.
10. Rosenfeld P J, et al. Ranibizumab for neovascular age-related macular degeneration. N Engl J Med. 2006; 355(14): 1419-1431.

11. Fletcher E C, Chong N V. Looking beyond Lucentis on the management of macular degeneration. Eye. 2008; 22(6):742-750.
12. Duch S, Buchacra O, Milla E, Andreu D, Tellez J. Intracameral bevacizumab (Avastin) for neovascular glaucoma: a pilot study in 6 patients. J Glaucoma. 2009; 18(2): 140-143.
13. Moraczewski A L, Lee R K, Palmberg P F, Rosenfeld P J, Feuer W J. Outcomes of treatment of neovascular glaucoma with intravitreal bevacizumab. Br J Ophthalmol. 2009; 93(5):589-593.
14. Dastjerdi M H, et al. Topical bevacizumab in the treatment of corneal neovascularization: results of a prospective, open-label, noncomparative study. Arch Ophthalmol. 2009; 127(4):381-389.
15. Jacobs D S, Lim M, Carrasquillo K G, Rosenthal P. Bevacizumab for corneal neovascularization. Ophthalmology. 2009; 116(3):592-593; author reply 593-594.
16. Oh J Y, Kim M K, Shin M S, Lee H J, Lee J H, Wee W R. The anti-inflammatory effect of subconjunctival bevacizumab on chemically burned rat corneas. Curr Eye Res. 2009; 34(2):85-91.
17. Ueno S, et al. Prolonged blockade of VEGF family members does not cause identifiable damage to retinal neurons or vessels. J Cell Physiol. 2008; 217(1): 13-22.
18. Salgaller M L. Technology evaluation: bevacizumab, Genentech/Roche. Curr Opin Mol Ther. 2003; 5(6):657-667.
19. Reichert J M, Valge-Archer V E. Development trends for monoclonal antibody cancer therapeutics. Nat Rev Drug Discov. 2007; 6(5):349-356.
20. Gerber H P, Ferrara N. Pharmacology and pharmacodynamics of bevacizumab as monotherapy or in combination with cytotoxic therapy in preclinical studies. Cancer Res. 2005; 65(3):671-680.
21. Ellis L M, Hicklin D J. VEGF-targeted therapy: mechanisms of anti-tumour activity. Nat Rev Cancer. 2008; 8(8):579-591.
22. Bergers G, Hanahan D. Modes of resistance to anti-angiogenic therapy. Nat Rev Cancer. 2008; 8(8):592-603.
23. Dorrell M I, Aguilar E, Scheppke L, Barnett F H, Friedlander M. Combination angio static therapy completely inhibits ocular and tumor angiogenesis. Proc Natl Acad Sci USA. 2007; 104(3):967-972.
24. Ratner M. Genentech discloses safety concerns over Avastin. Nat Biotechnol. 2004; 22(10): 1198.
25. Chen H X, Cleck J N. Adverse effects of anticancer agents that target the VEGF pathway. Nat Rev Clin Oncol. 2009; 6(8):465-477.
26. Bensussan A. BY55 (CD160). Protein Rev. Web. 2000; 1(72-73.
27. Anumantha A, et al. Cloning of BY55, a novel Ig superfamily member expressed on NK cells, CTL, and intestinal intraepithelial lymphocytes. J. Immunol. 1998; 161(6):2780-2790.
28. Fons P, et al. Soluble HLA-G1 inhibits angiogenesis through an apoptotic pathway and by direct binding to CD 160 receptor expressed by endothelial cells. Blood. 2006; 108(8):2608-2615.
29. Maeda M, et al. Murine CD 160, Ig-like receptor on NK cells and NKT cells, recognizes classical and non classical MHC class I and regulates NK cell activation. J. Immunol. 2005; 175(4426-4432.
30. Giuriato S, et al. Development of a conditional bio luminescent transplant model for TPM3-ALKinduced tumorigenesis as a tool to validate ALK-dependent cancer targeted therapy. Cancer Biol Ther. 2007; 6(8): 1318-1323.
31. Cursiefen C. Immune privilege and angiogenic privilege of the cornea. Chem Immunol Allergy. 2007; 92(50-57.
32. Smith L E, et al. Oxygen-induced retinopathy in the mouse. Invest Ophthalmol Vis Sci. 1994; 35(1): 101-111.
33. Economopoulou M, et al. Inhibition of pathologic retinal neovascularization by alpha-defensins. Blood. 2005; 106 (12):3831-3838.
34. Yu L, et al. Interaction between bevacizumab and murine VEGF-A: a reassessment. Invest Ophthalmol Vis Sci. 2008; 49(2):522-527.
35. Bock F, et al. Bevacizumab as a potent inhibitor of inflammatory corneal angiogenesis and lymphangiogenesis. Invest Ophthalmol Vis Sci. 2007; 48(6):2545-2552.
36. Habot-Wilner Z, Barequet I S, Ivanir Y, Moisseiev J, Rosner M. The inhibitory effect of different concentrations of topical bevacizumab on corneal neovascularization. Acta Ophthalmol. 2009.
37. Hashemian M N, Moghimi S, Kiumehr S, Riazi M, Amoli F A. Prevention and Treatment of Corneal Neovascularization: Comparison of Different Doses of Subconjunctival Bevacizumab with Corticosteroid in Experimental Rats. Ophthalmic Res. 2009; 42(2):90-95.
38. Hurmeric V, Mumcuoglu T, Erdurman C, Kurt B, Dagli O, Durukan A H. Effect of subconjunctival bevacizumab (Avastin) on experimental corneal neovascularization in guinea pigs. Cornea. 2008; 27(3):357-362.
39. Manzano R P, et al. Inhibition of experimental corneal neovascularisation by bevacizumab (Avastin). Br J Ophthalmol. 2007; 91(6):804-807.
40. Zhang Q, et al. Suppression of retinal neovascularization by the iNOS inhibitor aminoguanidine in mice of oxygen-induced retinopathy. Graefes Arch Clin Exp Ophthalmol. 2009; 247(7):919-927.
41. Passaniti A, et al. A simple, quantitative method for assessing angiogenesis and antiangiogenic agents using reconstituted basement membrane, heparin, and fibroblast growth factor. Lab Invest. 1992; 67(4):519-528.
42. Asselin-Paturel C, et al. Transfer of the murine interleukin-12 gene in vivo by a Semliki Forest virus vector induces B16 tumor regression through inhibition of tumor blood vessel formation monitored by Doppler ultrasonography. Gene Ther. 1999; 6(4):606-615.
43. Hamano Y, et al. Thrombospondin-1 associated with tumor microenvironment contributes to lowdose cyclophosphamide-mediated endothelial cell apoptosis and tumor growth suppression. Cancer Res. 2004; 64(5): 1570-1574.
44. Jain R. Normalization of tumor vasculature: an emerging concept in antiangiogenic therapy. Science. 2005; 307 (5706):58-62.
45. Jain R K, Munn L L, Fukumura D. Dissecting tumour pathophysiology using intravital microscopy. Nat Rev Cancer. 2002; 2(4):266-276.
46. Koehl G E, Gaumann A, Geissler E K. Intravital microscopy of tumor angiogenesis and regression in the dorsal skin fold chamber: mechanistic insights and preclinical testing of therapeutic strategies. Clin Exp Metastasis. 2009; 26(4):329-344.
47. Heymans O, Fissette J, Vico P, Blacher S, Masset D, Brouers F. Is fractal geometry useful in medicine and biomedical sciences? Med Hypotheses. 2000; 54(3):360-366.

48. Hamzah J, et al. Vascular normalization in Rgs5-deficient tumours promotes immune destruction. Nature. 2008; 453(7193):410-414.
49. Man S, et al. Antitumor effects in mice of low-dose (metronomic) cyclophosphamide administered continuously through the drinking water. Cancer Res. 2002; 62(10):2731-2735.
50. Greenberg J I, et al. A role for VEGF as a negative regulator of pericyte function and vessel maturation. Nature. 2008; 456(7223):809-813.
51. Padera T P, Stoll B R, Tooredman J B, Capen D, di Tomaso E, Jain R. Pathology: cancer cells compress intratumour vessels. Nature. 2004; 427(6976):695.
52. Lin M I, Sessa W C. Antiangiogenic therapy: creating a unique "window" of opportunity. Cancer Cell. 2004; 6(6):529-531.
53. Barakonyi A, et al. Cutting edge: engagement of CD 160 by its HLA-C physiological ligand triggers a unique cytokine profile secretion in the cytotoxic peripheral blood NK cell subset. J Immunol. 2004; 173(9):5349-5354.
54. Le Bouteiller P, et al. Engagement of CD 160 receptor by HLA-C is a triggering mechanism used by circulating natural killer (NK) cells to mediate cytotoxicity. Proc Natl Acad Sci USA. 2002; 99(16963-16968.
55. Ambati B K, et al. Corneal avascularity is due to soluble VEGF receptor-1. Nature. 2006; 443(7114):993-997.
56. Cao Y, Langer R. Optimizing the delivery of cancer drugs that block angiogenesis. Sci Transl Med. 2010; 2(15): 15psl3.
57. Makale M. Intravital imaging and cell invasion. Methods Enzymol. 2007; 426(375-401.
58. Elie N, Kaliski A, Peronneau P, Opolon P, Roche A, Lassau N. Methodology for quantifying interactions between perfusion evaluated by DCE-US and hypoxia throughout tumor growth. Ultrasound Med Biol. 2007; 33(4):549-560.
59. Wolfmger R, O'Connell M. Generalized linear mixed models: a pseudo-likelihood approach. J. Statist. Computation Stimul. 1993; 4(233-243.
60. Liang K Y, Zeger S L. Longitudinal Data Analysis Using Generalized Linear Models. Biometrika. 1986; 73(13-22).

The invention claimed is:

1. A method for treating neovascular eye diseases associated with neoangiogenesis, comprising administering an anti-CD160 antibody and an anti-VEGF antibody to a subject in need thereof, wherein said anti-CD160 antibody is the CL1-R2 monoclonal antibody or an antigen-binding fragment thereof.

2. The method according to claim 1, wherein said anti-CD160 antibody induces cell death of activated proliferating endothelial cells.

3. The method according to claim 1, wherein the administering of the anti-CD160 antibody and the anti-VEGF is simultaneous, separate or sequential.

4. The method according to claim 1, wherein the neovascular eye disease is selected from:
- all forms of corneal neovascularizations;
- all forms of choroidal neovascularizations and;
- all forms of retinal neovascularizations.

5. The method according to claim 1, wherein the subject is refractory to anti-VEGF treatment.

6. The method according to claim 1, wherein the anti-CD160 antibody is monoclonal antibody CL1-R2.

7. The method according to claim 1, wherein the antigen binding fragment of CL1-R2 is selected from the group consisting of a Fab, a Fab', a F(ab)2, F(ab')2 and dAb of CL1-R2.

8. The method according to claim 1, wherein the antigen binding fragment of CL1-R2 is selected from the group consisting of scFv, (scFv)2, diabody, multimeric scFv fused to a Fc fragment, and two Fabs bound face-to-tail.

9. The method according to claim 1, wherein the antibody or antigen binding fragment thereof is a monovalent or multivalent scFv.

10. The method according to claim 4, wherein the neovascular eye disease is selected from the group consisting of wet Age Related Macular Degeneration and neovascularization associated with proliferative diabetic retinopathy.

11. The method of claim 4, wherein the retinal neovascularizations comprise ischaemic retinopathies (IR).

12. The method of claim 4, wherein the choroidal neovascularizations comprise "wet" age-related macular degeneration (AMD).

13. The method of claim 4, wherein the anti-VEGF antibody is selected from the group consisting of bevacizumab and ranibizumab.

* * * * *